(12) United States Patent
Wright et al.

(10) Patent No.: US 6,660,291 B2
(45) Date of Patent: Dec. 9, 2003

(54) USE OF PAECILOMYCES SPP. AS PATHOGENIC AGENTS AGAINST SUBTERRANEAN TERMITES

(75) Inventors: Maureen S. Wright, New Orleans, LA (US); William J. Connick, Jr., New Orleans, LA (US); Mark A. Jackson, Peoria, IL (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/989,287

(22) Filed: Nov. 20, 2001

(65) Prior Publication Data

US 2003/0095951 A1 May 22, 2003

(51) Int. Cl.[7] .......................... A01N 25/32; A01N 63/04
(52) U.S. Cl. ...................... 424/406; 424/84; 424/93.5; 424/405; 424/DIG. 11; 435/254.1; 435/911
(58) Field of Search ............................... 424/405, 406, 424/411, 413, 84, 274.1, 93.5, DIG. 11, 254.1, 254.11, 911

(56) References Cited

U.S. PATENT DOCUMENTS

| | | | |
|---|---|---|---|
| 4,942,030 A | | 7/1990 | Osborne |
| 5,418,164 A | * | 5/1995 | Andersch et al. ........ 435/254.1 |
| 5,968,808 A | | 10/1999 | Jackson |
| 6,280,723 B2 | | 8/2001 | Stimac et al. |

FOREIGN PATENT DOCUMENTS

WO          94/04034      *   3/1994

OTHER PUBLICATIONS

Khaderkhan et al Muscardine Fungi—Insect. Sci. Applic. vol. 14 # 4 pp. 529–535, 1993.*

Delate, K.M. et al., "Potential use of pathogenic fungi in baits to control the Formosan subterranean termite (Isopt., Rhinotermitidae)," *J. Appl. Ent*. 119, pp. 429–433, 1995.

Culliney, T.W. et al., "Prospects for the biological control of subterranean termites (Isoptera: Rhinotermitidae), with special reference to *Coptotermes formosanus*," *Bulletin of Entomological Research 90*, pp. 9–21, 2000.

Milner, Richard J. et al., "Biological Control of Termites: Results and Experiences within a CSIRO Project in Australia," *Biocontrol Science and Technology* 6, pp. 3–9, 1996.

Khader Khan, H. et al., "Muscardine Fungi for the Biological Control of Agroforestry Termite *Odontotermes Obesus* (Rambur)," *Insect Sci. Applic*. vol. 14, No. 4, pp. 529–535, 1993.

Rath, Andrew, "Bio–Blast—A new Biological Tool for Your Termite Control Programs," *Pest Control*, vol. 63, pp. 42–43, 1995.

Jackson, Mark A. et al., "Liquid culture production of desiccation tolerant blastospores of the bioinsecticidal fungus *Paecilomyces fumosoroseus*," *Mycol. Res*. 101 (1), pp. 35–41, 1997.

\* cited by examiner

Primary Examiner—Neil S. Levy
(74) Attorney, Agent, or Firm—John D. Fado; Curtis P. Ribando

(57) ABSTRACT

The entomopathogenic fungus *Paecilomyces fumosoroseus* and certain related species, such as *P. javanicus* are useful for controlling infestations by subterranean termites, particularly those belonging to the family Rhinotermitidae. The family Rhinotermitidae includes two species of subterranean termites having extremely high economic importance in the United States; namely the Formosan subterranean termite (*Coptotermes formosanus* Shiraki), and the native (North American) subterranean termite (*Reticulitermes flavipes*). Large numbers of infectious propagules of the fungus, such as blastospores and conidia can be readily cultured on media that are easily and inexpensively prepared and incorporated into formulations for controlling termites. These fungi are useful for protecting living trees, plants, wood, wood structures, and other cellulosic materials susceptible to termite infestation and damage.

9 Claims, 8 Drawing Sheets

USE OF *PAECILOMYCES* SPP. AS PATHOGENIC AGENTS AGAINST SUBTERRANEAN TERMITES

BACKGROUND OF THE INVENTION

1. Field of the Invention

The invention relates to fungal compositions and methods of using them for control of subterranean termites.

2. Description of the Prior Art

Subterranean termites are particularly destructive pests in tropical and temperate regions throughout the world. In the United States alone, subterranean termites are estimated to cause $1 billion in damage annually including prevention and repair costs. They are known to infest cellulose-based materials including living trees, wooden structures, plant roots and books. One predominant species, the Formosan subterranean termite (FST), *Coptotermes formosanus* (Shiraki), has become an economically significant pest in the United States in the past 50 years. Reasons for this include their massive colonies which can contain tens of millions of individuals, their ability to attack several species of living trees, and their high level of reproduction. The Formosan subterranean termite is thought to have been transported to the US mainland at the end of World War II when military equipment was shipped back in wooden crates. The infestations have since radiated from the port cities of New Orleans and Lake Charles, La., Houston, Tex. and Charleston, S.C. The cryptic nature of the insects allowed them to establish colonies without being detected and made it difficult to determine the most effective treatment location. The extent of FST infestations has become apparent in dense swarms of flying termites and significant damage to buildings and trees.

Organochlorine compounds were previously used to control FST, but their sale was banned in 1988. Replacement chemicals are not as persistent [Su et al., *Pest Managem. Rev.* (1998) 3: 1–13]. In addition, by disturbing soil around a structure when landscaping or compensating for soil subsidence the chemical barriers can be compromised and allow FST access to the structure [Su et al., (1990) *Sociobiology* 17: 77–94]. Su et al. (1998, supra) review some alternative control methods including non-repellant termiticides and bait technology. In order for these techniques to work they must not repel termites, must be easily transferrable in or on termite bodies and have delayed toxicity which allows transfer from foraging workers to members of the termite colony that do not forage [*Sociobiology* (1996) 27: 253–275 and 1998, supra].

One alternative to chemical control entails use of biological control agents [Culliney et al., *Bulletin of Entomological Research* (2000) 90: 9–21]. Bacteria, viruses, protozoa and fungi have potential as pathogenic agents. Fungi exhibit qualities which can make them ideal for this application, including a slow-acting nature similar to that of successful chemicals, the ability to self-replicate and the ability of fungal spores to be spread by termite social behavior [Grace et al. (1992) *Sociobiology* 20: 23–28]. Milner et al. [*Biocontrol Science and Technology* (1966) 6: 3–9] review a wide variety of fungal pathogens that have been reported as potential pathogens to termites. Pathogenicity of strains of both *Metarhizium anisopliae* (Metschnikoff) Sorokin and *Beauveria bassiana* (Balsamo) Vuillemin have been demonstrated in laboratory colonies of *C. formosanus* [Delate et al. (1995) J. Appl. Entomol. 119:, 429–433; Wells et al. (1995) *J. Entomol. Sci.* 30: 208–215]. Jones et al. [Environ. Entomol. (1996) 25:, 481–487] discovered that small numbers of *B. bassiana* and *M. anisopliae* spores can be spread throughout a *C. formosanus* colony without being detected by the termites. Conditions in a termite nest, moderate temperature and high humidity, are conducive to the growth of fungal species and are important factors in fungal survivability and propagation [Kramm et al. (1982) *J Invertebr Pathol* 39: 1–5.; Ignoffo (1992) *Florida Entomol.* 75: 516–525]. Stimac et al. (U.S. Pat. No. 6,280,723) teach a novel *B. bassiana* strain (AATCC 20872) useful in controlling termites of the genera Cryptotermes, Coptotermes, Incistermes, and Reticulitermes. Grooming and other social activity between termites facilitate the spread of fungal infection throughout a colony, which may result in elimination of a colony or a drastic reduction in its numbers and potential to cause economic damage. However, defensive actions such as avoidance of fungi, the removal and burial of fungus-killed termite cadavers and various immune responses can limit the spread of infection in the colony.

Baits containing effective entomopathogenic agents may allow the "horizontal transmission" of a fungal pathogen from termite to termite and eventual spread to the entire colony. They would provide long-term control or suppression of termite infestations. The fungal isolate, dose, termite species and individual termite colony may all be factors that determine if there is repellency due to the presence of the fungus, and the degree of repellency. If spores are repellent, there will be less horizontal transmission. Bait formulation additives may be required to overcome the repellency.

It may be preferable that an entomopathogenic fungus intended for use as a biocontrol agent for termites have an effective, but relatively slow, mode of action. This will allow the fungus to become more widely dispersed throughout the colony before mortality occurs. A highly virulent fungus may only kill the termites in the immediate vicinity of the bait.

SUMMARY OF THE INVENTION

We have discovered strains of the entomopathogenic fungus of the genus Paecilomyces that are useful for control of infestations by subterranean termites, particularly those belonging to the family Rhinotermitidae, such as the Formosan subterranean termite and native North American subterranean termites. Large numbers of infectious propagules of the fungus can be readily cultured on media that are easily and inexpensively prepared. The entomopathogenic agents of particular interest are blastospores produced by *P. fumosoroseus* and closely related Paecilomyces spp.

In accordance with this discovery, it is an object of this invention to provide entomopathogenic fungi, compositions containing such fungi, and methods of using these fungi to kill subterranean termites and to protect wood susceptible to termite damage.

A specific objective of this invention is to control termite infestations using Paecilomyces spp.

Another objective of this invention is to provide a biologically-based alternative to currently available, chemical control methods for controlling subterranean termites.

Another specific objective of this invention is to control termite infestations with a formulation that is composed of an effective dose of infectious propagules of Paecilomyces in a suitable carrier for delivery to termites.

A further specific objective of this invention is to introduce a method of controlling termite infestations comprising delivery of a formulation of infectious propagules of Paecilomyces in, on, or near a currently or potentially infested structure, tree or plant.

Yet another specific objective of this invention is to provide a component of termite treatment strategies and formulations that will enhance control and reduce damage by termites. For instance, effective suppression of termite colonies may rely on an integrated pest management (IPM) strategy that would include the use of several strategies such as biological agents, chemicals, appropriate building techniques and physical barriers.

Other objectives and advantages of this invention will become readily apparent from the ensuing description.

DETAILED DESCRIPTION OF THE INVENTION

Figure 1:
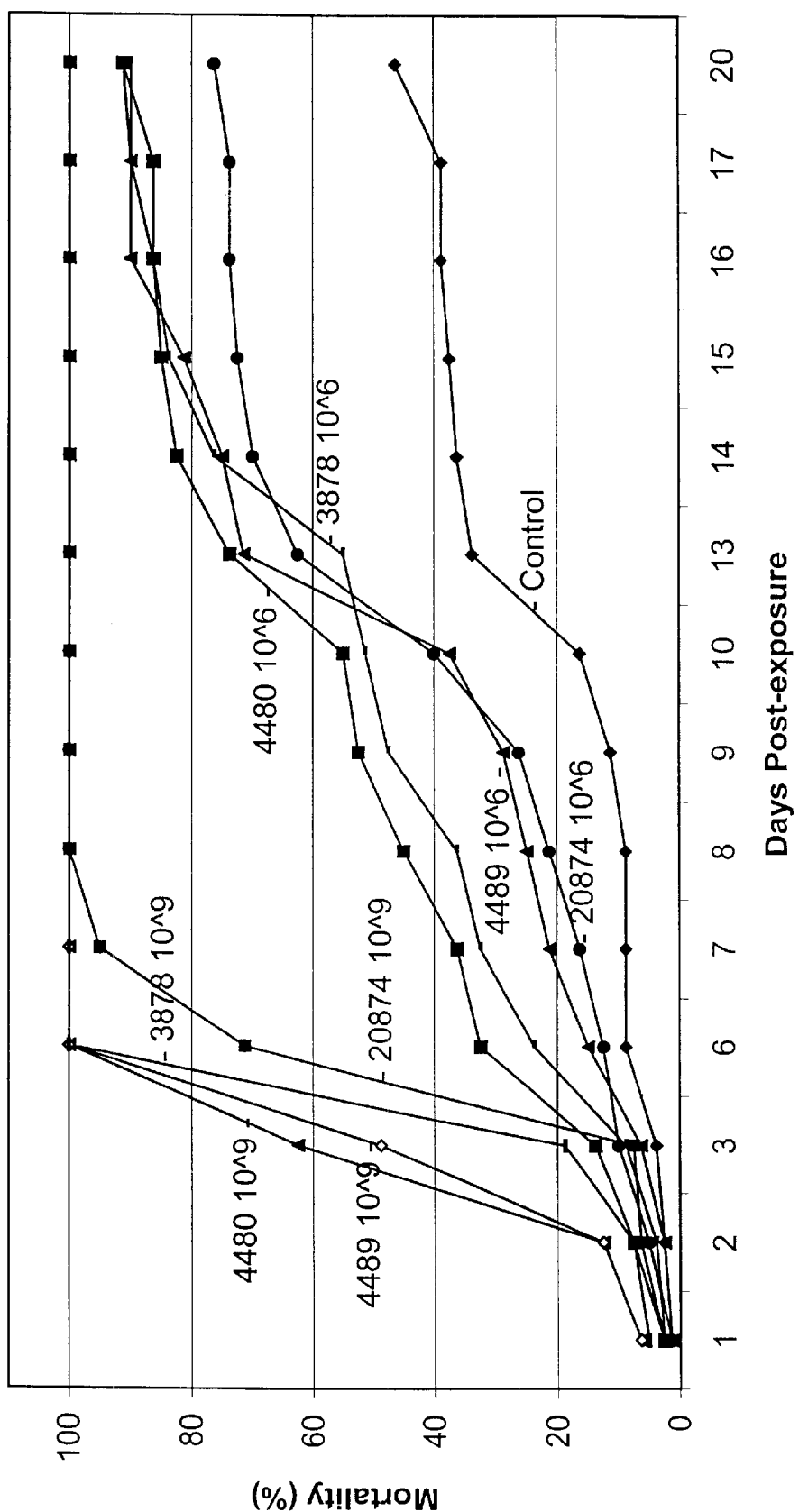
FIG. 1 is a series of graphs showing the percent mortality of Formosan subterranean termites as a function of the number of days post-exposure to filter paper wetted with various strains of *P. fumosoroseus* blastospores at either $1 \times 10^6$ or $1 \times 10^9$ blastospores/ml solution.

As used herein, the term "termiticide" refers to a material or mixture of materials which induce mortality, disrupt or impede growth, interfere with metamorphosis or other morphogenic functions, effect sterilization, or interfere with reproduction of the targeted termites. The term "controlling" is used herein to mean that the population is reduced, principally through mortality, at a level that is significantly greater than an untreated population. "Significant mortality" is defined herein to mean that the percentage of insects that die within a given period of time after coming into contact with the termiticide is significantly greater than the number of insects not contacted with the termiticide that die during the same period of time. An "effective amount" is used herein in reference to that quantity of entomopathogenic agent necessary to obtain significant mortality in a population or colony of termites. The actual rate amount of agent needed for a particular application will be dependent upon a number of factors, such as the mode of application, the environmental conditions, the particular fungal strain being used, the species of target termite, and the composition of the formulation. The person of ordinary skill in the art would be able to experimentally determine an actual effective amount for a particular situation by observing the success of a control regimen, and then modifying it accordingly. We have found that in petri dish assays described in the Examples, below, effective control can be achieved by causing termites to directly or indirectly come into contact with a substrate treated with a suspension containing from about $1 \times 10^6$ to about $1 \times 10^9$ viable propagules/ml.

The fungal entomopathogens of the invention include any of variety of strains of *P. fumosoroseus* or closely-related species, such as *P. javanicus*, that are effective in controlling subterranean termites, that is, in causing significant mortality in a population of termites. Exemplary strains of *P. fumosoroseus*, without limitation thereto, include ARSEF 4480, ARSEF 3581, ARSEF 3878, ARSEF 4489, ARSEF 4491, and ATCC 20874. An exemplary strain of *P. javanicus* is ARSEF 322. ARSEF accessions are freely available from the U.S. Department of Agriculture, Agricultural Research Service Entomopathogenic Fungus collection, Tower Road, Ithaca, N.Y. 14853-2901.

The fungal entomopathogens encompassed herein are effective for use against subterranean termite species, particularly those belonging to the family Rhinotermitidae, and more particularly against the Formosan termite (*Coptotermes formosanus*) and native North American termites (*Reticulitermes flavipes*). Other target Rhinotermitidae species of potential economic interest include *R. hesperus*, and *R. virginicus*. Unlike the higher termites of the Termitidae family that have bacteria in their guts for digesting cellulosic materials, the Rhinotermitidae and other lower termites rely on gut-dwelling protozoa for this process.

Infection of termite individuals with the Paecilomyces spp. is effected by application of a control agent comprising fungal propagules directly to termites, to the locus of termites, to material susceptible to termite infestation, or to the locus of material susceptible to termite infestation. Treatment areas may include woody environments such as lumber, structures or buildings constructed at least in part from wood, dead or living plants, particularly trees, forests, orchards or other agricultural fields which are subject to termite attack.

The preferred propagules of interest are spores (i.e. blastospores), and particularly dessication tolerant blastospores as described by Jackson in U.S. Pat. No. 5,968,808, herein incorporated by reference. The blastospores described by Jackson are produced in a liquid culture medium. Also contemplated by the invention are control agents comprising primarily Paecilomyces spp. blastospores in combination with Paecilomyces spp. conidia and/or mycelia. These may be applied to the treatment area in the form of a recovered culture broth or in combination with a suitable vehicle or carrier that does not substantially interfere with the viability of the fungus.

Subterranean termites are normally attracted to and reliant upon the presence of moisture; therefore, water is a particularly preferred carrier, although other carriers suitable for use herein include but are not limited to alcohols, ethers, glycols, ketones, esters, and solid carriers such as clays, silicas, cellulosics, rubber, or synthetic polymers. It may also be desirable to incorporate a humectant, such as methylcellulose or polyacrylamide, to maintain the moisture content in the composition. The Paecilomyces-containing pesticidal compositions of this invention may, for example, be formulated as wettable powders, dusts, granules, baits, solutions, emulsifiable concentrates, emulsions, suspension concentrates and sprays (aerosols).

The fungal entomopathogens of the invention may be applied to, or impregnated into, a bait matrix intended to be placed in bait stations. The matrices that have potential for use in bait stations in accordance with the invention would include solids, semi-solids, or liquids. The bait stations are usually placed at least partially below the soil surface, but may also be completely above ground. It has been found that placement of a bait station in the path of an active mud tube is effective for achieving contact of the bait matrix by the termites. When the station is in the vicinity of a termite colony, termites will preferentially feed on the treated bait, and thereafter transfer the entomopathogen to other members of the colony. The matrix will usually contain a form of cellulose as an attractant. Suitable cellulose-containing materials for use as bait matrices include, but are not limited to paper, paper products (e.g., virgin paper, recycled paper, or a combination of both), cotton linter, cardboard, paperboard, wood, sawdust, wood particles or wood flour, processed or purified cellulose, cellulose derivatives such as cellulose ethers, and including, for example, methylcellulose, hydroxypropylmethyl-cellulose, and hydroxybutylmethylcellulose, or other agricultural fibers. Bait matrices may also contain other organic materials that provide nutrition, attractant or arrestant properties. A particularly preferred bait matrix for use herein is described by Rojas et al. (commonly assigned U.S. patent application Ser. No. 09/294,499, filed Apr. 20, 1999, and Ser. No. 09/625,940, filed Jul. 26, 2000), the contents of which are incorporated by reference herein.

The Paecilomyces spp. entomopathogens described above may be used alone or in combination with other (secondary) termiticides. Suitable secondary termiticides include, but are not limited to, biological controls such as termite growth regulators, and materials or organisms that are toxic to termites (i.e., toxicants) such as chemical insecticides, pathogenic nematodes, other fungi, protozoans, or bacteria. Preferred secondary termiticides are slow-acting (i.e., killing exposed termites after hours, days or weeks), to reduce "avoidance" effects before individuals have infected other members of the colony with the P. fumosoroseus. A variety of slow-acting termiticides are known in the art, and include, for example silafluofen, borates (boric acid, disodium octaborate tetrahydrate), sulfluramid and other fluoroalkyl sulfonamides, avermectin, hydramethylnon, hexaflumuron and other chitin synthesis inhibitors and other acyl ureas, diflubenzuron (Dimilin), azadirachtin, dechlorane (Mirex), diiodomethyl-para-tolyl sulfone (A-9248), fluorosulfonates, imidacloprid, azadirachtin, cyromazine, juvenile hormones and juvenile hormone mimics or analogs such as fenoxycarb, methoprene, hydroprene, triprene, furnesinic acid ethyl and alkoxy derivatives, and pyriproxyfen (Nylar), and the plant *Rheuneo jupanic* Thunb. Roth. The mortality rate of otherwise faster-acting insecticides may be retarded by microencapsulation or other slow-release formulation. Biological control agents that may be used as secondary termiticides include fungi such as *Metarhizium anisopliae,* *Aspergillus flavus,* and *Beauveria bassiania,* nematodes such as *Neoplectana carpocapsae,* insect viruses, pathogenic bacteria such as *Bacillus thuringiensis* and *Serratia marcescens,* and toxins derived from biological control agents such as *B. thuringiensis* toxin.

Optionally, the Paecilomyces-containing compositions may be further formulated with other insect attractants such as pheromones of the target termites or termite extracts containing pheromones or pheromone mimics. Termite pheromones suitable for use herein are generally well-known in the art, and include, for example, (Z,Z,E)-3,6,8-dodecatrien-1-ol, and the aggregation pheromone n-hexanoic acid. The composition may also include one or more additional termite attractants such as food odor attractants or aggregation attractants. Without being limited thereto, suitable food odor attractants are described by Peterson (U.S. Pat. No. 5,756,114), the contents of which are incorporated by reference herein.

The following Examples are intended only to further illustrate the invention and are not intended to limit the scope of the invention, which is defined by the claims.

EXAMPLES

Propagation of Paecilomyces Strains

Fungi used in the following Examples included *P. fumosoroseus:* ARSEF 3581 (host: *Bemisia argentifolli;* McAllen, Tex.); ARSEF 4480 (*Bemisia tabaci;* Calexico, Calif.); ARSEF 4489 (*Bemisia tabaci;* Calexico, Calif.); ARSEF 4491 (*Bemisia tabaci;* Padappai, India); ATCC 20874 (*Bemisia tabaci*); and ARSEF 3878 (*Bemisia tabaci;* Multan, Pakistan). *P. javanicus* ARSEF 322 (*Litodactylus leucogaster;* Gainesville, Fla.) was also tested.

Conidia. Stock cultures of all isolates were grown on potato dextrose agar (PDA) for three weeks at room temperatures, cut into 1 mm$^2$ agar plugs and stored in 10% glycerol at $-80°$ C. Conidial inocula were produced by inoculating Potato Dextrose Agar (PDA; DIFCO) plates with a conidial suspension from frozen stock cultures and growing these cultures at room temperature ($\sim25°$ C.) for 2–3 wks. In Formosan subterranean termite bioassays where conidia were tested, conidia were obtained from sporulated PDA plates.

Blastospores. Blastospores of *P. fumosoroseus* were produced for termite bioassays as follows. Liquid cultures (100 mL in 250 mL baffled, Erlenmeyer flasks) were grown at 28° C. and 300 rpm in a rotary shaker incubator (INNOVA 4000, New Brunswick Scientific, Edison, N.J., USA). Blastospore precultures were inoculated with a final concentration of $1\times10^5$ conidia/mL with conidia obtained from sporulated PDA plates of *P. fumosoroseus*. After three days growth, blastospores obtained from these precultures were used to inoculate production flasks at a final concentration of $5\times10^6$ blastospores/mL. Blastospore production flasks were harvested after three days growth.

Spore concentrations were determined microscopically with a hemacytometer. A minimum of triplicate flasks were used for all treatments and all experiments were repeated at least twice.

Paecilomyces Media Composition

The basal component of the liquid culture medium contained per liter: $KH_2PO_4$, 2.0 g; $CaCl_2.2H_2O$, 0.4 g; $MgSO_4.7H_2O$, 0.3 g; $CoCl_2.6H_2O$, 37 mg; $FeSO_4.7H_2O$, 50 mg; $MnSO_4.H_2O$, 16 mg; $ZnSO_4.7_2O$, 14 mg; thiamin, riboflavin, pantothenate, niacin, pyridoxamine, thioctic acid, 500 µg each; folic acid, biotin, vitamin $B_{12}$, 50 µg each. Carbon and nitrogen were provided in the medium by addition of glucose (Sigma Chemical, St. Louis, Mo.), 80 g/L, and Casamino acids (vitamin-assay, Difco, Detroit, Mich.), 25 g/L. All media had an initial pH of 5.5 and pH was uncontrolled during culture growth. Glucose stock solutions were autoclaved separately.

Desiccation of *P. fumosoroseus* Blastospores

Blastospores were air-dried using two filter aids; diatomaceous earth or calcined kaolin clay. Experiments designed to determine the repellency of spore preparations to termite tunneling were conducted with spore/diatomaceous earth preparations. All other experiments were conducted with spore/clay formulations. All air-dried *P. fumosoroseus* spore preparations were obtained by mixing liquid cultures of *P. fumosoroseus*, which consisted primarily of blastospores, with either diatomaceous earth (HYFLO, Celite Corp., Lompoc, Calif.) or calcined hydrophilic kaolin clay (Surround, Engelhard Corp., Iselin, N.J., USA). These filter aids were added to whole cultures of *P. fumosoroseus* at a rate of 1 gram diatomaceous earth or kaolin clay for each $2 \times 10^{10}$ blastospores. Spore/filter aid preparations were vacuum-filtered on filter paper (Whatman No. 1) to remove the excess liquid and the filter cake obtained was dried overnight in a humidity-controlled drying chamber (RH>60) to 2–5% moisture. The moisture content of the dried blastospore preparations, expressed as (wet weight-dry weight)/wet weight×100, was determined with a moisture analyzer (MARK I, Denver Instruments, Tempe, Ariz., USA). Dried blastospore preparations were stored under vacuum in nylon/EVOH/polyethylene bags with a desiccant (1 g silica packet; #Z16356-Z, Sigma, St. Louis, Mo.) at 4° C. The viability of dried *P. fumosoroseus* spore preparations was determined using a previously described spore germination assay [Jackson, M. A. et al. (1997) *Mycol. Res.* 101:35–41, herein incorporated by reference] for diatomaceous earth preparations and by plate counting for spore preparations containing kaolin clay.

Collection of Termites

Formosan subterranean termites (*Coptotermes formosanus* Shiraki) and Native subterranean termites (*Reticulitermes flavipes*) were obtained from colonies at the Southern Regional Research Center, City Park and the University of New Orleans which are all located in New Orleans, La. Multiple colonies of termites were chosen to prevent colony vitality biasing of data. Each colony represented one replicate in each experiment. Bucket traps were established to allow access to termites. Twenty workers of at least 3rd instar (as determined by size) were used in each of the replicates.

Exposure of Termites to Fungi

For Mortality Determination Only: Either 10 or 20 Formosan subterranean termites from each of four colonies were allowed to walk on fungal cultures for 5 minutes. These workers were then transferred to 100×15 mm Petri dishes (Falcon, Franklin Lakes, N.J.) which contained Whatman #4 filter paper (Maidstone, England), dampened with sterile water (Solution 2000 Water Purification System, Solution Consultant Inc., Jasper, Ga.).

For Transferability and Mortality Determination: Ten Formosan subterranean termites from each of four colonies were allowed to walk on fungal cultures for 5 minutes. These workers were then transferred to 100×15 mm Petri dishes (Falcon, Franklin Lakes, N.J.) which contained Whatman #4 filter paper (Maidstone, England), dampened with sterile water (Solution 2000 Water Purification System, Solution Consultant Inc., Jasper, Ga.), and 10 unexposed worker termites from the same colony as those exposed to the fungus.

Incubation of Exposed Termites and Controls

All plates containing termites were then placed in an unlit incubator at 25° C. and 99% humidity for the duration of the experiment. Control plates were incubated as described above and contained the same number of termites as the test plates, none of which had been exposed to fungal cultures. All work prior to incubation was conducted under a laminar flow hood (NuAire, Plymouth, Minn.).

Example 1

Mortality of FST by *P. fumosoroseus* (Four Strains) Blastospores.

Twenty FST (*Coptotermes formosanus* Shiraki) workers from each of four colonies were incubated on filter paper that was wetted with 500 μL of a $1 \times 10^6$ or $1 \times 10^9$ blastospores/ml solution of *P. fumosoroseus* strains ARSEF 4480, ARSEF 4489, ARSEF 3878, or ATCC 20874. Controls were exposed to filter paper wetted with water only. The percent mortality as a function of days post-exposure for each trial is shown in FIG. 1.

Example 2

Mortality of the FST by *P. fumosoroseus* (Two Strains) Blastospores.

Figure 2:
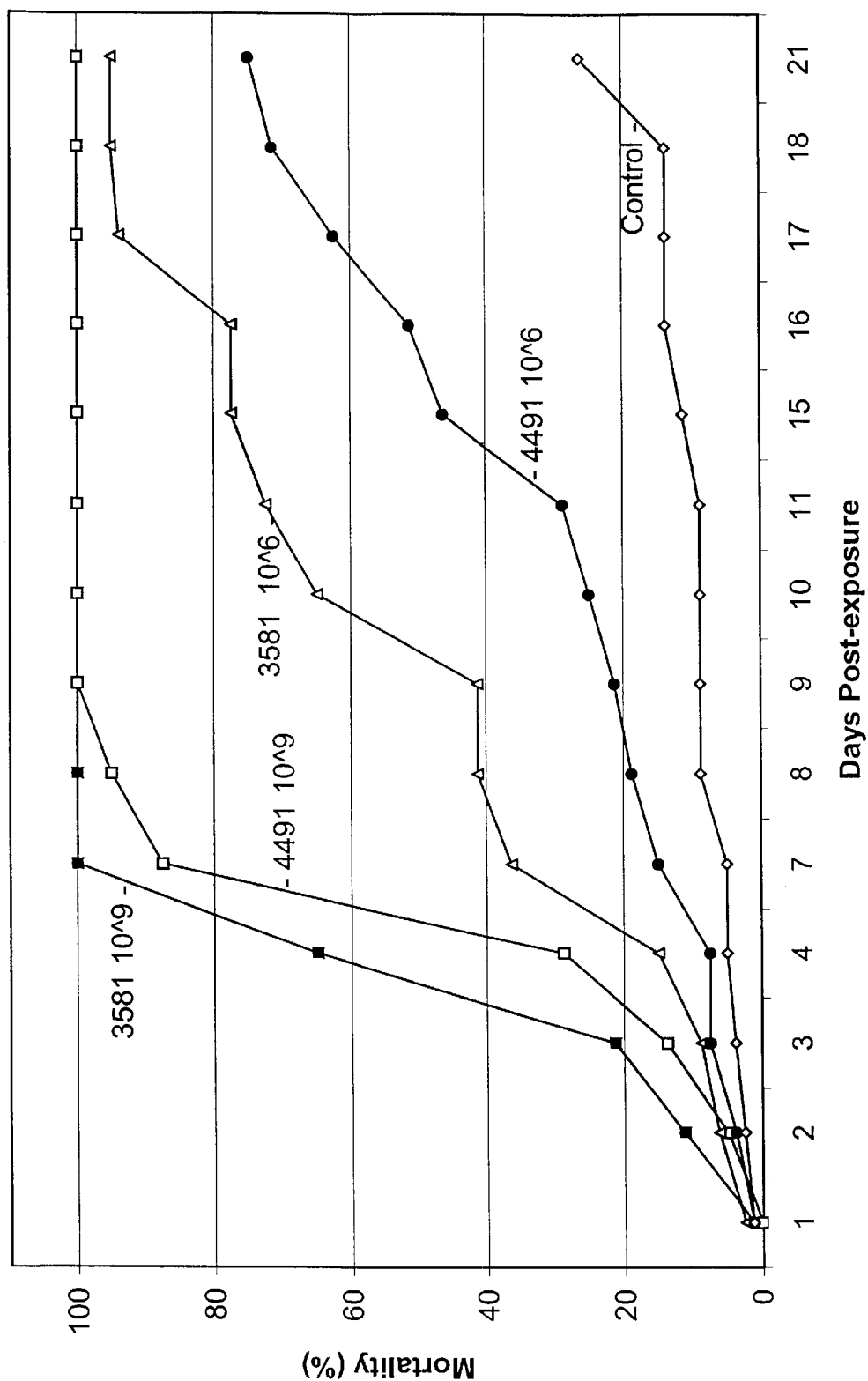
FIG. 2 is a series of graphs showing the percent mortality of Formosan subterranean termites as a function of the number of days post-exposure to filter paper wetted with various additional strains of *P. fumosoroseus* blastospores at either $1 \times 10^6$ or $1 \times 10^9$ blastospores/ml solution.

Twenty FST (*Coptotermes formosanus* Shiraki) workers from each of four colonies were incubated on filter paper that was wetted with 500 μL of a $1 \times 10^6$ or $1 \times 10^9$ blastospores/ml solution of *P. fumosoroseus* strains ARSEF 3581 and ARSEF 4491. Controls were exposed to filter paper wetted with water only. The percent mortality as a function of days post-exposure for each trial is shown in FIG. 2.

Example 3

Mortality of the FST by *P. fumosoroseus* Strain ARSEF 3581 Blastospores.

Figure 3:
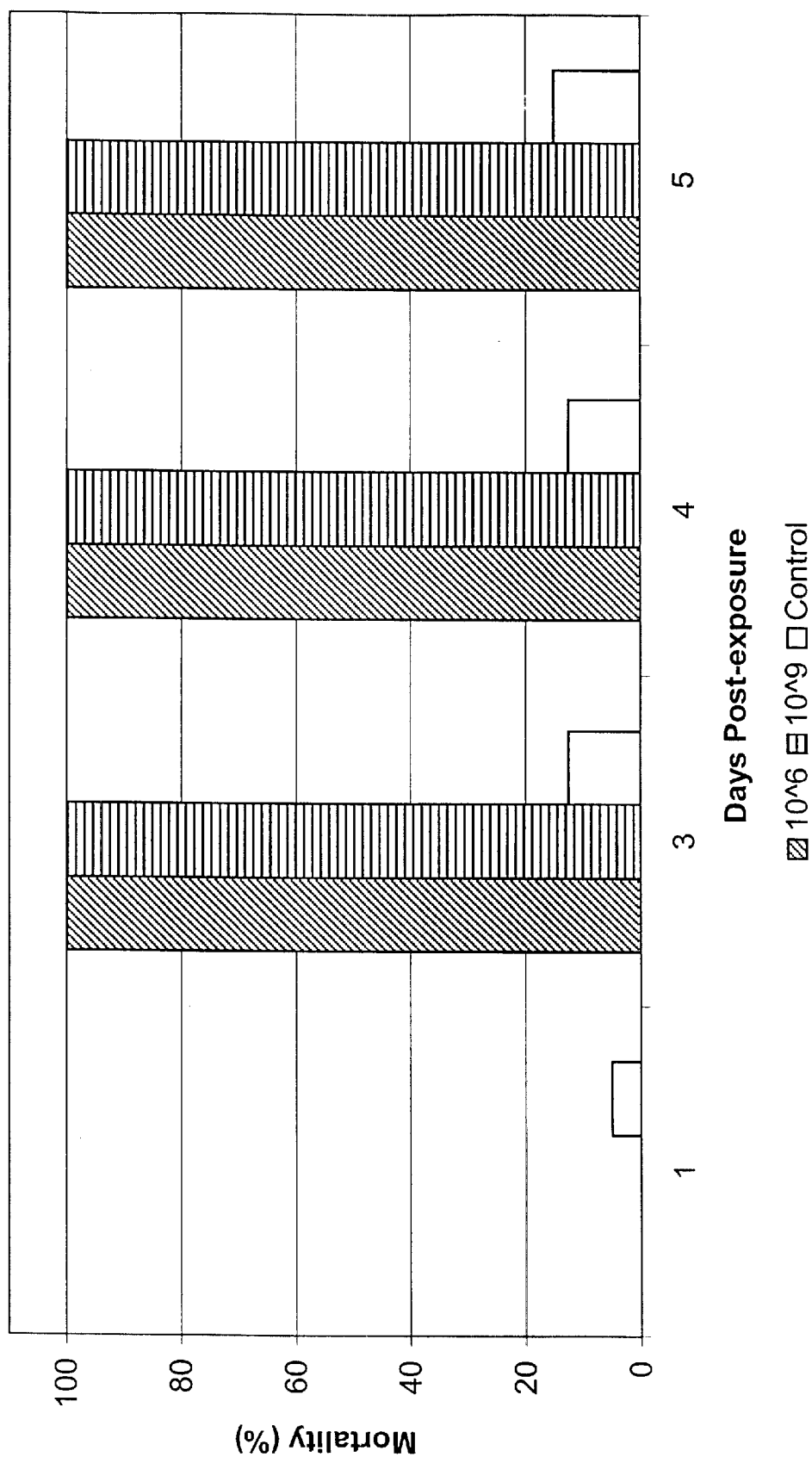
FIG. 3 is a series of bar graphs showing the percent mortality of Formosan subterranean termites as a function of the number of days post-exposure to filter paper wetted with *P. fumosoroseus* strain ARSEF 3581 blastospores at either $1 \times 10^6$ or $1 \times 10^9$ blastospores/ml solution.

Twenty FST (*Coptotermes formosanus* Shiraki) workers from each of four colonies were incubated on filter paper that was wetted with 500 μL of a $1 \times 10^6$ or $1 \times 10^9$ blastospores/ml solution of *P. fumosoroseus* strain ARSEF 3581. Controls were exposed to filter paper wetted with water only. The percent mortality as a function of days post-exposure for each trial is shown in FIG. 3.

Example 4

Mortality of the FST by *P. fumosoroseus* Strain ARSEF 3581, Blastospores Stored as Whole Cultures for 9 Days at 4° C.

Figure 4:
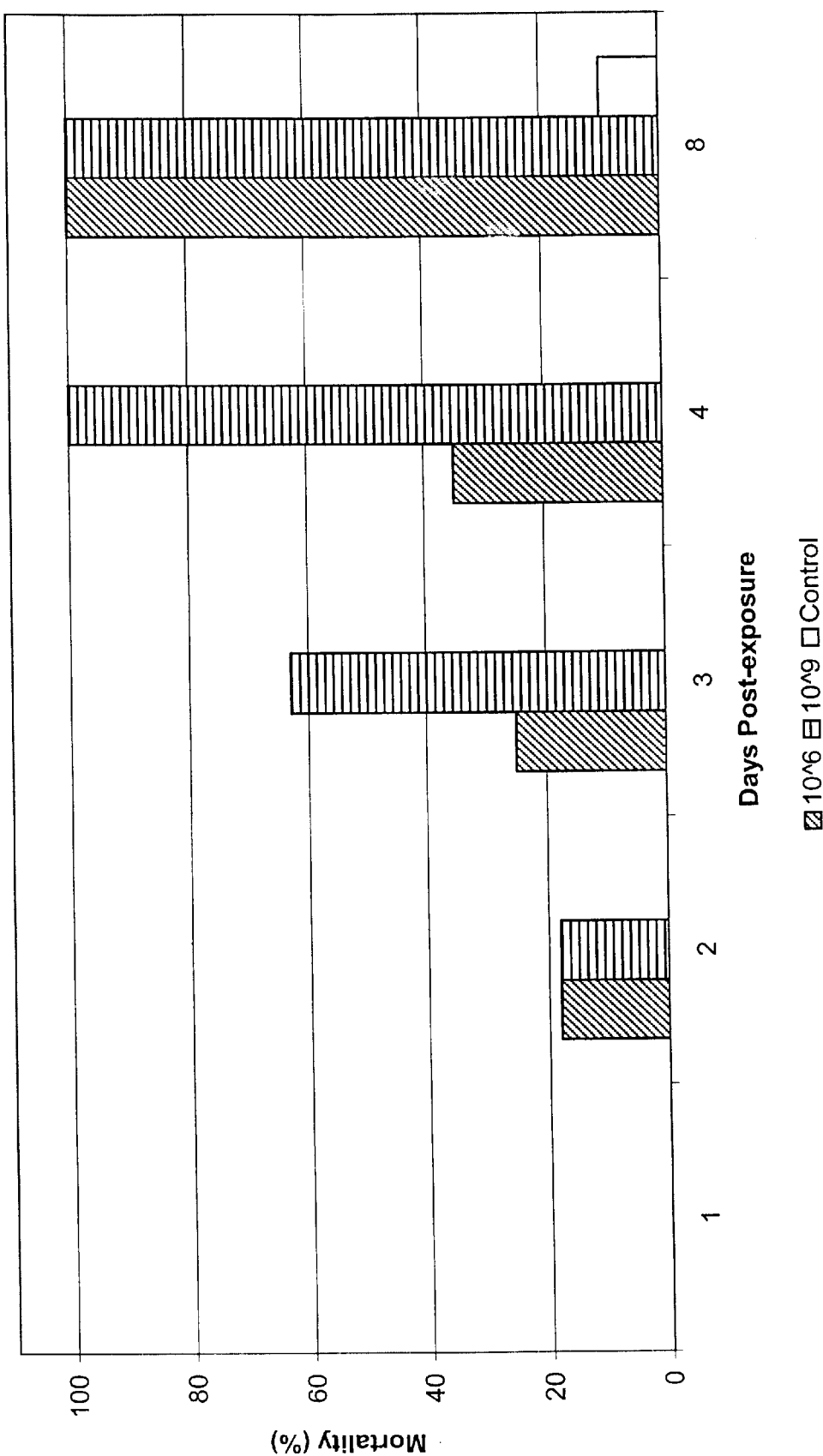
FIG. 4 is a series of bar graphs showing the percent mortality of Formosan subterranean termites as a function of the number of days post-exposure to filter paper wetted with 9-day old blastospores of *P. fumosoroseus* strain ARSEF 3581 at either $1 \times 10^6$ or $1 \times 10^9$ blastospores/ml solution.

Twenty FST (*Coptotermes formosanus* Shiraki) workers from each of four colonies were incubated on filter paper that was wetted with 500 μL of a $1 \times 10^6$ or $1 \times 10^9$ blastospores/ml solution of *P. fumosoroseus* strain ARSEF 3581 as in Example 3, but the blastospores were stored at 4° C. for an additional 9 days. Controls were exposed to filter paper wetted with water only. The percent mortality as a function of days post-exposure for each trial is shown in FIG. 4.

Example 5

Mortality of the Native Subterranean Termite by *P. fumosoroseus* Strain ARSEF 3581 Blastospores.

Figure 5:
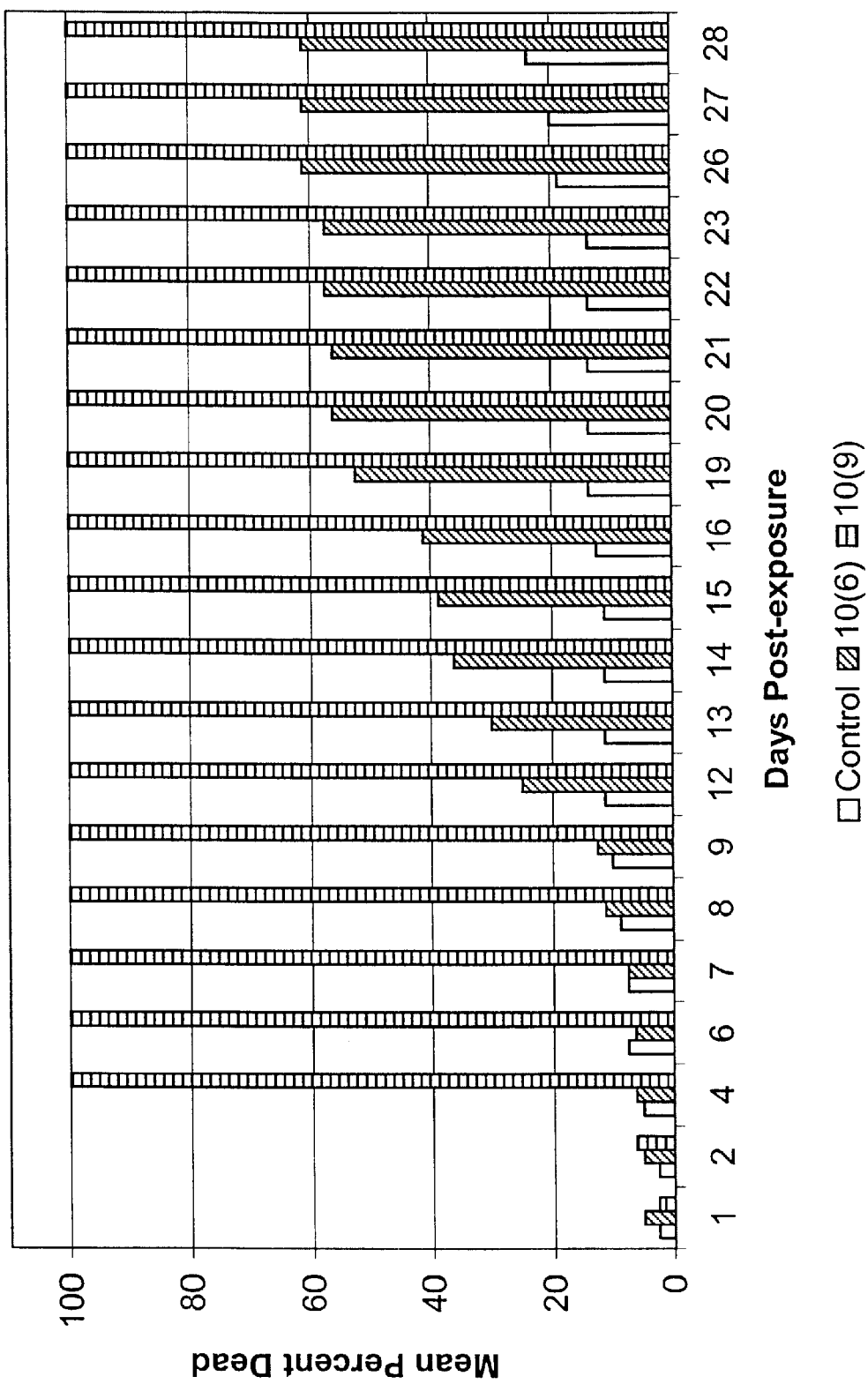
FIG. 5 is a series of bar graphs showing the mean percent mortality of Native subterranean termites as a function of the number of days post-exposure to filter paper wetted with *P. fumosoroseus* strain ARSEF 3581 blastospores at either $1 \times 10^6$ or $1 \times 10^9$ blastospores/ml solution.

Twenty Native Subterranean termites (*Reticulitermes flavipes*) workers from each of four colonies were incubated on filter paper that was wetted with 500 μL of a $1 \times 10^6$ or $1 \times 10^9$ blastospores/ml solution of *P. fumosoroseus* strain ARSEF 3581. Controls were exposed to filter paper wetted with water only. The percent mortality as a function of days post-exposure for each trial is shown in FIG. 5.

Example 6
Mortality of the Native Subterranean Termite by *P. javanicus* ARSEF 322 Conidia.

Figure 6:
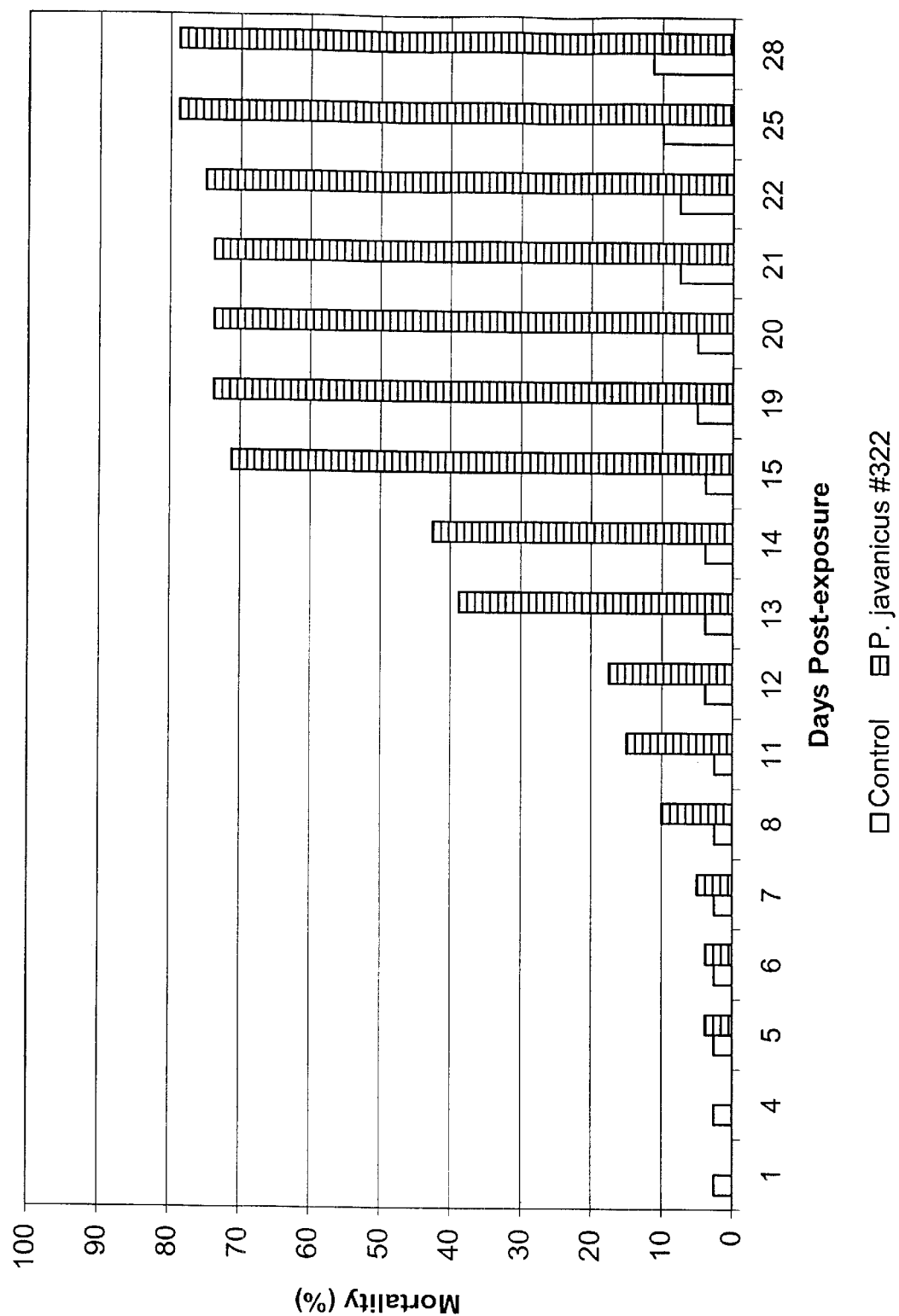
FIG. 6 is a series of bar graphs showing the collective mortality of Native subterranean termite workers exposed to a conidial culture on an agar plate of *P. javanicus* strain ARSEF 322 and nestmates of the workers to which the fungi were transferred.

Ten Native Subterranean termite (*Reticulitermes flavipes*) workers from each of four colonies were allowed to walk on a conidial culture of *P. javanicus* ARSEF 322 on agar plates for 5 minutes. The exposed subjects were then incubated with an equal number of nest-mates on filter paper that was kept moist with water. Controls were exposed to filter paper wetted with water only. The percent mortality as a function of days post-exposure is shown in FIG. 6.

Example 7
Transferability and Mortality of FST by Paecilomyces spp. Conidia.

Figure 7:
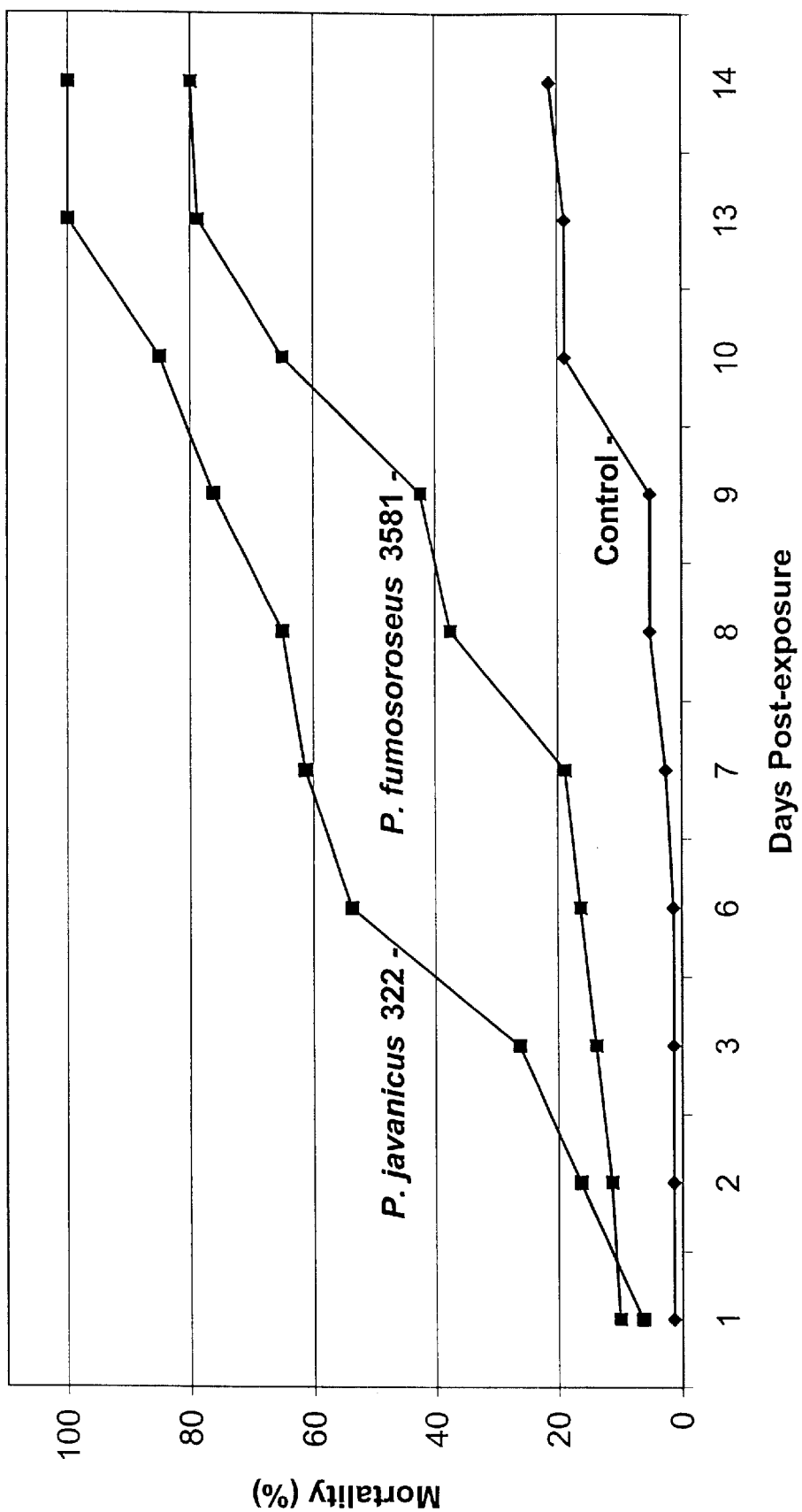
FIG. 7 shows the collective mortality of Formosan subterranean termite workers directly exposed to conidial culture on an agar plate of either *P. javanicus* strain ARSEF 322 or *P. fumosoroseus* strain ARSEF 3581 and nestmates of the workers to which the fungi were transferred.

Ten FST workers from each of 4 colonies were allowed to walk on a conidial culture of either *P. javanicus* ARSEF 322 or *P. fumosoroseus* strain ARSEF 3581 on an agar plate for 5 minutes. The exposed subjects were then incubated with an equal number of nest-mates on filter paper that was kept moist with water. Controls were allowed to walk on uninoculated agar then incubated on filter paper that was kept moist with water. Mortality rates in excess of 50% indicate that the fungus was transferred from the exposed workers to nest-mates that were not directly exposed to the fungus. The percent mortality as a function of days post-exposure for each trial is shown in FIG. 7.

Example 8
Transferability and Mortality of FST by *P. fumosoroseus* Conidia.

Figure 8:
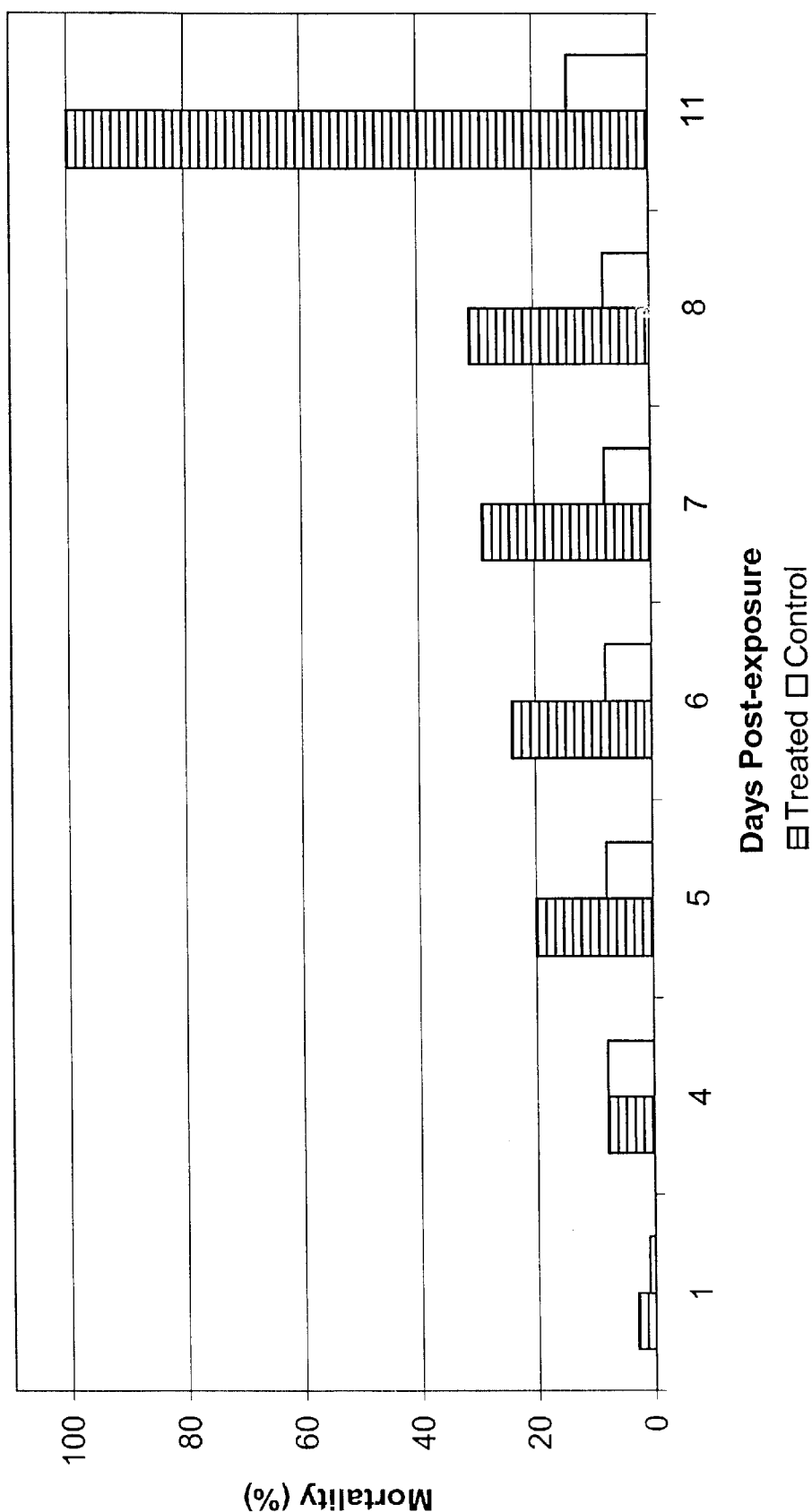
FIG. 8 shows the collective mortality of Formosan subterranean termite workers directly exposed to conidial culture on an agar plate of *P. fumosoroseus* strain ARSEF 3581 and nestmates of the workers to which the fungi were transferred.

Ten FST workers from each of 4 colonies were allowed to walk on a conidial culture of *P. fumosoroseus* strain ARSEF 3581 on an agar plate for 5 minutes. The exposed subjects were then incubated with an equal number of nest-mates on filter paper that was kept moist with water. Controls were allowed to walk on uninoculated agar and then incubated on filter paper that was kept moist with water. Mortality rates in excess of 50% indicate that the fungus was transferred from the exposed workers to nest-mates that were not directly exposed to the fungus. The percent mortality as a function of days post-exposure for each trial is shown in FIG. 8.

Example 9
Control of FST Using Dust, Spray, and Bait Formulations Containing *P. fumosoroseus*.

This experiment was performed to test formulations containing *P. fumosoroseus* that are examples of dusts, sprays, and baits. The mortality of FST was determined as a function of time after treatment. Termites from 4 colonies were treated to reduce errors caused when only a single colony is used. Except as indicated, the procedures and conditions of this experiment were the same as those indicated for Examples 1–8, above.

The experiment consisted of 13 treatments×4 colonies×10 termites (9 workers and 1 soldier) per petri plate for a total of 52 plates (520 termites total: 130 from each of 4 colonies). Plates were stored in a plastic container with a lid. The container was lined with wet paper towels to maintain 100% RH, and was kept in an incubator at 28° C. in the dark. The results are shown in Table I, below.

Materials:

A *P. fumosoroseus* 3581 blastospore suspension grown in liquid culture that contained $1.6 \times 10^9$ cfu/ml (Treatments 9E & 9J).

*P. fumosoroseus* 3581 dried blastospores in a diatomaceous earth (1 part) and rice flour (9 parts) mixture that contained $3.4 \times 10^9$ cfu/g (Treatment 9A).

A *P. fumosoroseus* 3581 conidial suspension (conidia washed from Sabouraud Dextrose Maltose Agar plates with sterile 0.01% Tween 80 solution) that contained $2.4 \times 10^7$ cfu/ml (Treatments 9H & 9L).

*P. fumosoroseus* 3581 conidia that were grown on rice flour in a vented polypropylene bag for 7 weeks at 25° C. with a daily 12-h photoperiod. The *P. fumosoroseus*-infested rice flour contained $7.7 \times 10^7$ cfu/g (Treatment 9C).

The diatomaceous earth was Hyflo SuperCel. Rice flour was autoclaved twice before use. Spent liquid media was filtered to remove fungal propagules for use as a control. Filter paper was Whatman #1, 8.2-cm diameter. Tween 80 (Polysorbate 80) was obtained from Uniqema R&T, Wilmington, Del.

Termite mortality at 5 and 10 days was determined and the number of termites located on treated and untreated halves in the bait experiment (Treatments 9J–9M) were recorded at days 1 and 2.

Formulations:

Dusts

Dusting procedure: For treatments 9A–9D, 10 termites from each colony were dusted with a small amount of the treatment by shaking gently. The termites were transferred to a petri plate that contained 1 sheet of filter paper dampened with 1.0 ml of sterile water.

Sprays

For treatments 9E–9I, 10 termites from each colony were sprayed with each treatment formulation. The sprayed termites were then transferred to a petri plate that contained one sheet of filter paper moistened with 1.0 ml sterile water.

Baits

For treatments 9J–9M, 0.5 ml of blastospore suspension or conidial suspension was applied to a one-half sheet of paper in a petri plate. A 0.5-ml volume of sterile water was applied to another one-half sheet placed in the same dish. The sheets were actually cut a little less than in half in order to leave a gap of about 2 mm between them. Ten termites from each colony were exposed to each treatment. Controls consisted of filtrate from blastospore suspension (fungal propagules removed) and a 0.01% Tween 80 solution.

Example 10
Evaluation of Termite Repellency by *P. fumosoroseus*.

The possibility of a termiticide being repellent to the target insect and creating an avoidance response is a concern. The repellent properties of *P. fumosoroseus* isolate 3581 toward FST, or the lack thereof, were evaluated by the procedure of Staples and Milner [*Sociobiology* 36(1): 133–148, (2000)] which was modified by the use of laboratory-grade sand instead of river sand and by the use of 5% agar instead of 2% agar. The increase of agar concentration improved the ability of the termites to tunnel into the agar layer.

In brief, the referenced agar-tube method for quantifying the repellency of a fungus to termites involved a 35-mm deep layer of sand treated with the fungus and placed in the bottom of a 50-ml plastic centrifuge tube. The sand was topped with a 32-mm layer of water agar. The sand was dampened with either water or a suspension of fungal propagules in water to a final water content of about 10% to 12%. A 0.04-g strip of filter paper was placed on top of the agar as a food source. A total of 50 FST termites (40 workers and 10 soldiers) were added to the top of the agar. The test consisted of three tubes per treatment. Three termite colonies (one colony in each of the three tubes) were used in order to reduce error due to differences in colony response to exposure to the fungus. Both blastospores and conidia of *P. fumosoroseus* were tested in the form of liquid and solid treatments and the appropriate untreated controls were included in the experiment. The depth of penetration of the termites into the sand substrate was measured at 2, 3, and 7 days and the results were expressed as a percentage of the total depth of the sand layer (Table II). The concentrations of the fungus in the damp sand substrate were as follows: blastospores in liquid treatment=$4.9\times10^7$ cfu/g; blastospores in solid treatment=$4.8\times10^8$ cfu/g; conidia in liquid treatment=$1.9\times10^6$ cfu/g; and conidia in solid treatment=$1.2\times10^7$ cfu/g.

It may be concluded from the data in Table II that blastospores and conidia of *P. fumosoroseus* isolate 3581 applied as a suspension in water to sand did not repel the termites. The termites tunneled into the treated sand and reached the bottom of the tube by 7 days as they did in untreated sand. However, when blastospores and conidia were incorporated in the sand as dry preparations (blastospores in diatomaceous earth and conidia grown on rice flour) and the sand/fungus mixture was dampened with water, repellency occurred in both treatments. The repellency was more pronounced in the case of the conidia/rice flour preparation. In contrast, the termites had completely penetrated the untreated sand by the second day of the experiment.

The results of this experiment suggest that repellency may be minimized by the type of preparation used to apply the fungus (for example, liquid or solid preparations) and by the particular propagules chosen (for example, blastospores or conidia). The concentration of the fungus in the soil is another factor which may allow control of the degree of repellency of the fungus to termites.

TABLE I

Mortality of FST Caused by Dust, Spray, and Bait Formulations Containing *P. fumosoroseus* 3581

| Example | Treatment | Termite Mortality, % (Days after treatment) 5 | 10 |
|---|---|---|---|
| DUSTS | | | |
| 9A | P. fr. blastospores in diatom. earth/rice flour | 73 | 100 |
| 9B | Control: ditom. earth/rice flour | 13 | 35 |
| 9C | P. fr. conidia in infested rice flour | 100 | 100 |
| 9D | Control: rice flour | 3 | 8 |
| SPRAYS | | | |
| 9E | P. fr. blastospore suspension | 100 | 100 |
| 9F | Control: filtrate from blastospore suspension | 5 | 38 |
| 9G | Control: liquid media | 20 | 30 |
| 9H | P. fr. conidia washed from plates | 83 | 100 |
| 9I | Control: 0.01% Tween 80 | 5 | 8 |
| BAITS | | | |
| 9J | P. fr. blastospores on filter paper | 83 | 100 |
| 9K | Control: filtrate from blastospore suspension | 20 | 73 |
| 9L | P. fr. conidia on filter paper | 65 | 100 |
| 9M | Control: 0.01% Tween 80 | 0 | 5 |

The results of the formulation experiment with dusts, sprays, and baits showed that significant numbers of termites were being killed by the *P. fumosoroseus* treatments by 5 days and all the termites treated with the fungus were killed by 10 days. Additionally, the results of the bait treatments (9J–9M) showed that there was no repellency caused by the *P. fumosoroseus* at day one. At day two, the blastospores showed a mild repellency to the termites (40% were on the treated and 60% were on untreated paper) as did the conidia (28% were on the treated and 52% were on the untreated paper) (Data not shown in table).

TABLE II

Repellency of Termite by *P. formosoroseus*

| Treatment | % Penetration of Treated Sand 2 Days | 3 Days | 7 Days |
|---|---|---|---|
| Liquid treatments | | | |
| Blastospores (liquid culture) | 79 | 90 | 100 |
| Conidia (washed from plates) | 61 | 97 | 100 |
| Control (water) | 52 | 67 | 100 |
| Solid treatments | | | |
| Blastospores in diatomaceous earth | 27 | 33 | 89 |
| Control (diatomaceous earth) | 100 | 100 | 100 |
| Conidia in rice flour | 7 | 7 | 7 |
| Control (rice flour) | 100 | 100 | 100 |

We claim:

1. A method for controlling subterranean termites of the family Rhinotermitidae comprising applying to said termites, to the locus of said termites, to material susceptible to said termite infestation, or to the locus of material susceptible to said termite infestation an amount of blastospores and/or conidia of Paecilomyces spp. effective to infect and kill said termites, wherein said Paecilomyces spp. is selected from the group consisting of *P. fumosoroseus* and *P. javanicus.*

2. The method of claim 1, wherein said subterranean termites are of a species selected from the group consisting of *Coptotermes formosanus* Shiraki, *Reticulitermes flavipes, Reticulitermes virginicus*, and *Reticulitermes hesperus.*

3. The method of claim 1, wherein said Paecilomyces spp. is *P. fumosoroseus.*

4. The method of claim 1, wherein said Paecilomyces spp. is *P. javanicus.*

5. The method of claim 1, wherein said Paecilomyces spp. is applied in the form of dessication tolerant blastospores.

6. The method of claim 1, wherein said material susceptible to said termite infestation is a wood-containing structure.

7. The method of claim 1, wherein said material susceptible to said termite infestation is a termite bait station.

8. The method of claim 1, wherein said material susceptible to said termite infestation is a dead or living plant.

9. The method of claim 1, wherein said material susceptible to said termite infestation is a living tree.

* * * * *